(12) United States Patent
Sun et al.

(10) Patent No.: US 6,768,009 B1
(45) Date of Patent: Jul. 27, 2004

(54) N-HALAMINE VINYL COMPOUNDS AND THEIR POLYMERIC BIOCIDES

(75) Inventors: Gang Sun, Davis, CA (US); YuYu Sun, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/535,348

(22) Filed: Mar. 24, 2000

(51) Int. Cl.⁷ .............................................. C07D 235/02
(52) U.S. Cl. .............................. 548/301.1; 548/301.4; 548/317.1
(58) Field of Search .................... 548/317.1, 301.1, 548/301.4

(56) References Cited

U.S. PATENT DOCUMENTS

| | | | |
|---|---|---|---|
| 3,285,928 A | 11/1966 | Gubitz | |
| 3,876,657 A | 4/1975 | Aelony | |
| 3,971,757 A | 7/1976 | Rasberger | |
| 4,091,223 A | 5/1978 | Zussman et al. | |
| 4,241,208 A | 12/1980 | Susumo et al. | |
| 5,459,145 A | 10/1995 | Saccomano et al. | |
| 5,714,127 A | 2/1998 | DeWitt et al. | |
| 5,882,357 A | 3/1999 | Sun et al. ................ | 8/189 |
| 6,020,491 A | 2/2000 | Tay-Yuan et al. | |
| 6,077,319 A | 6/2000 | Sun et al. ................ | 8/189 |

FOREIGN PATENT DOCUMENTS

| | | |
|---|---|---|
| DE | 19 00 169 A | 9/1969 |
| DE | 89 846 A | 5/1972 |
| DE | 24 37 916 A | 2/1976 |
| DE | 24 37 917 A | 2/1976 |
| DE | 27 34 618 A | 2/1978 |
| EP | 0 240 370 A | 10/1987 |
| WO | WO 94 20118 A | 9/1994 |
| WO | WO 96 08949 A | 3/1996 |

OTHER PUBLICATIONS

Pedregal et al., Journal of Heterocyclic Chemistry (Mar.–Apr. 1984), 21(2), pp. 477–480.*
Database CA Online Chemical Abstracts Service, Columbus, Ohio US; Piottukh Peletsky, V. N. et al., "Which IR search system is better for selection of unknown structure analogues?" retrieved from STN Database accession No. 131:294929 XP002185900 compoun with RN=37732–87–9 & *Anal. Chim. Acta*, 396(1):99–103 (1999).

Database CA Online! Chemical Abstracts Service, Columbus, Ohio, US; Oooka, Masataka et al., "Water–based ciuable urea resin compositions" retrieved from STN Database accession No. 123:259950 XP002185901 abstract & JP 07 102209 A(Dainippon Ink & Chemicals, Japan), Apr. 18, 1995.
Database CA Online! Chemcial Abstracts Service, Columbus, Ohio, US; Aelony, David et al., "Aminiomides. IX. General synthesis of 1–substituted–2–imidazolidinones" retreived from STN Database accession No. 77:88393 XP002185902 compound with RN=37732–87–9 & *J. Heterocycl. Chem.*, 9(3)687–90 (1972).
Database CA Online! Chemical Abstracts Service, Columbus, Ohio, US; Hennion, George F. et al., "Substituted acetylenes. LXXXVI. Synthesis and reactions of some polysubstituted 2–imidazolidinones" retrieved from STN Database accession NO. 67:90720 XP002185903 compound with RN=13584–71–9 & *J. Org. Chem.* 32(9):2819–22 (1967).
Database CA Online! Chemical Abstracts Service, Columbus, Ohio, US; Mar. 26, 2000 Sun, YuYu et al., "Novel N–halamine polymeric biocides: synthesis and antibacterial activity of hydantoin–containing polymers" retrieved from STN Database accession No. 133:79161 XP002185904 abstract & *Polym. Prepr.* (*Am. Chem. Soc., Div. Polym Chem.*) 41(1):270 271 (2000).
Sun, YuYu et al., "Novel regenerable N–halamine polymeric biocides. I. Synthesis, characterization, and antibacterial activity of hydantoin–containing polymers" *J. Appl. Polym. Sci.*, 80(13):2460–2467 (2001) XP002185899.
Pedergal C et al., "Etude de Quelques Derives N–3–Substitues Et N–1,N–3 Disubstitues Dela Cyclohexanosphirohydantoine" Journal of Heterocyclic Chemistry, Heterocorporation. Provo, US, vol. 21, Apr. 1984, pp. 477–480, XP002918458 ISSN: 0022/152X compound 2d.

* cited by examiner

*Primary Examiner*—Laura L. Stockton
(74) *Attorney, Agent, or Firm*—Townsend and Townsend and Crew LLP

(57) ABSTRACT

The present invention provides heterocyclic vinylic compounds that can be used to form biocidal polymers. The polymers thus generated can used alone or can be grafted onto textiles, fabrics and polymers. The polymers are readily converted to N-halamine structures on exposure to a halogen source such as commercially available chlorine bleach. The N-halamine derivatives exhibit potent antibacterial properties against microoganisms and these properties are durable and regenerable.

9 Claims, 9 Drawing Sheets

N-HALAMINE VINYL COMPOUNDS AND THEIR POLYMERIC BIOCIDES

FIELD OF THE INVENTION

This invention relates to heterocyclic vinylic amines reagents useful for the preparation of biocidal polymers. The biocidal polymers are usefull for generating medical and hygienic-use textiles.

BACKGROUND OF THE INVENTION

Contamination of polymeric materials by microorganisms such as pathogenic bacteria, odor-generating bacteria, molds, fungi and viruses is of great concern in the medical industry, the food and restaurant industries, as well as in consumer products. Survival of microorganisms on polymeric materials and transfer of these microorganisms between patients and health care workers (HCWs) has been demonstrated, and it is widely accepted that hospital gowns, patient drapes, carpeting and bedding materials, etc., can be elements in cross-infections. (see, Lidwell, O. M. et al., *J Appl. Bact.* 37:649 (1974)); Rubbo, S. D. and Saunders, J., *J Hyg. Camb.*, 61:507 (1963); Ransjo, U., *J. Hyg. Camb.*, 82:369 (1979); and Hambraeus, A., *J. Hyg. Camb.*, 71:799 (1973)). Medical gowns and uniforms currently in use provide barriers for HCWs, but have proven to be ineffectual in studies by numerous researchers. (see, for example, Beck, W. C. and Collette, T. S., *Am. J. Surg.*, 83:125 (1952); Smith, J. W. and Nichols, R. L. *Arch. Surg.*, 126:756 (1991); Lovitt, S. A. et al., *Am. J. Infect. Control,* 20:185 (1992); Quebbeman, E. J. et al., *Annal. Surg.,* 214:614 (1991); Granzow, J. W. et al., *Am. J. Infect. Control,* 26:85 (1998)).

The occurrence of contaminated cleaning cloths in domestic applications has also been investigated. Results from several different studies indicate that more than half of the investigated dish cloths and cleaning cloths were contaminated by one or more of the following organisms: *Escherichia coli, Staphylococcus aureus, Streptococcus faecahis* and *Clostridium perfringens* (see, Scott, E. et al., *J. Hyg. Camb.*, 89:279 (1982); Tebutt, C. M., *J. Hyg. Camb.,* 97:81 (1986); and Scott, E. et al., *J. Appl. Bact.,* 68:271 (1990)). Further studies show that wiping hard surfaces with contaminated cloths can result in contamination of hands, equipment and other surfaces. (see, Mackintosh, C. A. and Hoffman, P. N. *J. Hyg. Camb.,* 92:345 (1984)).

These findings suggest that biocidal properties should be an effective feature of medical and related healthcare and hygienic-use textiles. In general, hygenic-use textiles are made of synthetic polymers, and polymeric biocides have been reviewed by several researchers recently. (see, Vigo, T. L. (R. B. Seymour and R. S. Porter, Eds.), *Manmade Fibers: Their Origin and Development,* Elsevier Appl. Sci., p. 214 (1992); Vigo, T. L. (Gebelein, C. and Carraher, C., Eds.), *Biotechnology and Bioactive Polymers,* Plenum Press, p. 225 (1994); Worley, S. D. and Sun, G., *Trends Polym. Sci.,* 11:364 (1996)).

Among the currently investigated biocidal materials, N-halamines have been shown to provide almost instant and total kill of a wide range of microorganisms. (see, Worley, S. D. et al., *Trends Polym. Sci.,* 11:364 (1996)). There are many advantages associated with using N-halamine structures. First, they are stable in long-term use and storage over a wide temperature range. Second, they are regenerable when activity is lost due to normal use patterns. (see, Sun, G. et al., *Polymer,* 37:3753 (1996); Worley, S. D. et al., *The Polymeric Materials Encyclopedia,* 1, A-B, p. 550 (1996); Sun, G. et al. *Water Res. Bull.,* 1996, 32:793 (1996)). More recently, N-halamine materials have been incorporated into cellulose-containing fabrics. (see, Bickert, J. R. et al., *International Conference on Safety & Protective fabric '98,* 1998, p 1; Sun, G. et al., *Textile Chem. Colorist,* 6:26 (1998); Sun, G. et al., *Textile Chem. Colorist,* 31:21 (1999)). Results indicate that as little as 1% (wt) add-on of halamine structures provides powerful biocidal efficacy (6–7 log reduction) against the most common pathogens, at a contact time of two minutes.

U.S. Pat. No. 5,882,357, issued to Sun et al., on Mar. 16, 1999, discloses durable and regenerable microbiocidal textiles and methods for preparing the same. The microbiocidal textiles are prepared using a wet finishing process to covalently attach a heterocyclic N-halamine to a cellulose-based material or other polymeric material. The biocidal activity of the textiles can be regenerated by washing with a halogenated solution. In addition, U.S. Pat. No. 6,020,491, issued to Wonley et al., on Feb. 1, 2000, discloses cyclic amine monomers and polymers that are used to form biocidal N-halamine polymers. The polymers are useful as disinfectants for potable water, swimming pools, hot tubs, industrial water systems, cooling towers, air-conditioning systems, and the like.

In spite of the advances in the prior art, there remains a need for new monomeric units useful for generating polymers having microbiocidal activity. Polymers that can be used to generate microbiocidal fabrics, rubbers, plastics, paints, coatings, and articles are also needed. The present invention fulfills these and other needs.

SUMMARY OF THE INVENTION

In certain embodiments, the present invention provides heterocyclic vinylic amines that can be readily polymerized with most acrylic, substituted-acrylic and vinyl monomers. The polymers thus generated exhibit biocidal efficacy after exposure to a halogen source, such as chlorine bleach. Moreover, their antibacterial properties are durable and regenerable. As such, the present invention provides a compound having the formula

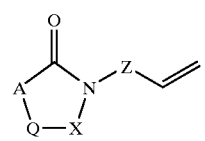

I

In Formula I, A is a functional group including, but not limited to, NH, N—$R^8$ and $CR^1R^2$, wherein $R^8$ is a halogen $R^1$ and $R^2$, in Formula I are each a functional group including, but not limited to, optionally substituted ($C_1$–$C_6$) alkyl, optionally substituted ($C_2$–$C_6$)alkenyl, optionally substituted ($C_2$–$C_6$)alkynyl, optionally substituted cycloalkyl, optionally substituted ($C_1$–$C_6$)alkoxy, optionally substituted aryl and optionally substituted heteroaryl.

In an alternative embodiment, $R^1$ and $R^2$ and the carbon to which they are bound, join to form an optionally substituted carbocyclic or optionally substituted heterocyclic ring.

In Formula I, Q is a functional group including, but not limited to, C(O), NH, N—$R^9$ and $CR^3R^4$, wherein $R^9$ is a halogen. $R^3$ and $R^4$, in Formula I are each a functional group including, but not limited to, optionally substituted ($C_1$–$C_6$) alkyl, optionally substituted ($C_2$–$C_6$)alkenyl, optionally substituted ($C_2$–$C_6$)alkynyl, optionally substituted cycloalkyl, optionally substituted ($C_1$–$C_6$)alkoxy, optionally substituted aryl and optionally substituted heteroaryl.

In an alternative embodiment, $R^3$ and $R^4$ and the carbon to which they are bound, join to form an optionally substituted carbocyclic or optionally substituted heterocyclic ring.

In Formula I, X is a functional group including, but not limited to, C(O)—$NR^5$ and $CR^6R^7$, wherein $R^5$ is a functional group including, but not limited to, hydrogen, halogen, optionally substituted ($C_2$–$C_6$)alkenyl and optionally substituted ($C_1$–$C_6$)alkyl. $R^6$ and $R^7$, in Formula I, are each a functional group including, but not limited to, optionally substituted ($C_1$–$C_6$)alkyl, optionally substituted ($C_2$–$C_6$)alkenyl, optionally substituted ($C_2$–$C_6$)alkynyl, optionally substituted cycloalkyl, optionally substituted ($C_1$–$C_6$)alkoxy, optionally substituted aryl and optionally substituted heteroaryl;

In an alternative embodiment, $R^6$ and $R^7$ and the carbon to which they are bound, join to form an optionally substituted carbocyclic or optionally substituted heterocyclic ring.

Z, in Formula I, is a functional group including, but not limited to, optionally substituted ($C_1$–$C_3$)alkylene, C(O), or a single bond. When Z is a single bond, a vinyl group is bonded directly to the ring nitrogen.

In another embodiment, the present invention provides a polymer comprising a mixture of monomeric units having the formulae

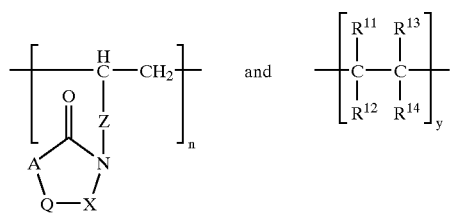

In Formula II, A is a functional group including, but not limited to, NH, N—$R^8$ and $CR^1R^2$, wherein $R^8$ is a halogen. $R^1$ and $R^2$, in Formula II, are each a functional group including, but not limited to, optionally substituted ($C_1$–$C_6$) alkyl, optionally substituted ($C_2$–$C_6$)alkenyl, optionally substituted ($C_2$–$C_6$)alkynyl), optionally substituted cycloalkyl, optionally substituted ($C_1$–$C_6$)alkoxy, optionally substituted aryl and optionally substituted heteroaryl.

In an alternative embodiment, $R^1$ and $R^2$ and the carbon to which they are bound, join to form an optionally substituted carbocyclic or optionally substituted heterocyclic ring.

In Formula II, Q is a functional group including, but not limited to, C(O), NH, N—$R^9$ and $CR^3R^4$, wherein $R^9$ is a halogen.

$R^3$ and $R^4$, in Formula II are each a functional group including, but not limited to, $R^3$ and $R^4$, optionally substituted ($C_1$–$C_6$)alkyl, optionally substituted ($C_2$–$C_6$)alkenyl, optionally substituted ($C_2$–$C_6$)alkynyl, optionally substituted cycloalkyl, optionally substituted ($C_1$–$C_6$)alkoxy, optionally substituted aryl and optionally substituted heteroaryl.

In an alternative embodiment, $R^3$ and $R^4$ and the carbon to which they are bound, join to form an optionally substituted carbocyclic or optionally substituted heterocyclic ring.

In Formula II, X is a functional group including, but not limited to, C(O)—$NR^{10}$ and $CR^6R^7$, wherein $R^{10}$ is a functional group including, but not limited to, hydrogen, halogen, optionally substituted ($C_2$–$C_6$)alkenyl and optionally substituted ($C_1$–$C_6$)alkyl.

$R^6$ and $R^7$, in Formula II, are each a functional group including, but not limited to, optionally substituted ($C_1$–$C_6$) alkyl, optionally substituted ($C_2$–$C_6$)alkenyl, optionally substituted ($C_2$–$C_6$)alkynyl, optionally substituted cycloalkyl, optionally substituted ($C_1$–$C_6$)alkoxy, optionally substituted aryl and optionally substituted heteroaryl.

In an alternative embodiment, $R^6$ and $R^7$ and the carbon to which they are bound, join to form an optionally substituted carbocyclic or optionally substituted heterocyclic ring.

Z, in Formula I, is a functional group including, but not limited to, optionally substituted ($C_1$–$C_3$)alkylene, C(O), or a single bond.

$R^{11}$ in Formula II, is a functional group including, but not limited to, hydrogen, halogen, hydroxyl, cyano, ($C_1$–$C_6$) alkyl, ($C_2$–$C_6$)alkenyl, ($C_1$–$C_6$)alkoxy, ($C_1$–$C_6$) alkylcarbonyl, ($C_1$–$C_6$)alkylcarboxyl, aldehydo, amido, aryl and heterocyclyl.

$R^{12}$ in Formula II, is a functional group including, but not limited to, hydrogen, halogen, hydroxyl, cyano, ($C_1$–$C_6$) alkyl, ($C_2$–$C_6$)alkenyl, ($C_1$–$C_6$)alkoxy, ($C_1$–$C_6$) alkylcarbonyl, ($C_1$–$C_6$)alkylcarboxyl, aldehydo, amido, aryl and heterocyclyl.

$R^{13}$ in Formula II, is a functional group including, but not limited to, hydrogen, halogen, hydroxyl, cyano, ($C_1$–$C_6$) alkyl, ($C_2$–$C_6$)alkenyl, ($C_1$–$C_6$)alkoxy, ($C_1$–$C_6$) alkylcarbonyl, ($C_1$–$C_6$)alkylcarboxyl, amido, aldehydo, aryl and heterocyclyl.

$R^{14}$ in Formula II, is a functional group including, but not limited to, hydrogen, halogen, hydroxyl, cyano, ($C_1$–$C_6$) alkyl, ($C_2$–$C_6$)alkenyl, ($C_1$–$C_6$)alkoxy, ($C_1$–$C_6$) alkylcarbonyl, ($C_1$–$C_6$)alkylcarboxyl, aldehydo, amido, aryl and heterocyclyl. The index "x" is an integer from 1 to 250 inclusive. The index "y" is an integer from 1 to 250 inclusive.

In yet another embodiment, the present invention provides a polymer comprising a polymeric unit of the formula:

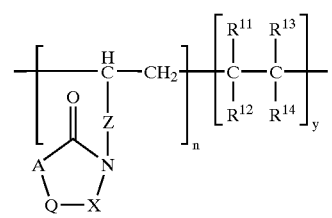

wherein A, Q, X, Z, $R^1$, $R^2$, $R^3$, $R^4$, $R^6$, $R^7$, $R^8$, $R^9$, $R^{10}$, $R^{11}$ $R^{12}$, $R^{13}$, $R^{14}$, "n" and "y" have been defined above. In this embodiment. The polymer comprises a least one unit having a dimmer wherein "n" is 1 and "y" is 1.

In still yet another embodiment, the present invention provides a method for making a polymer, comprising: admixing a compound having the formula

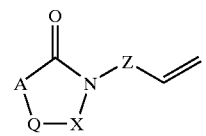

wherein A, Q, X, Z, $R^1$, $R^2$, $R^3$, $R^4$, $R^5$, $R^6$, $R^7$, $R^8$, and $R^9$ have been defined above, with a with a vinyl monomer in a reaction mixture thereby making a polymer.

In another embodiment, the present invention provides a method for chemically modifying a polymer, comprising: admixing the polymer in a reaction mixture with a compound having the formula he formula

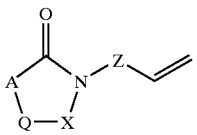

wherein A, Q, X, Z, $R^1$, $R^2$, $R^3$, $R^4$, $R^5$, $R^6$, $R^7$, $R^8$, and $R^9$ have been defined above, with a vinyl monomer in a reaction mixture thereby chemically modifying the polymer.

In certain aspects, a hydantoin-containing monomer such as 3-allyl-5,5- dimethylhydantoin, are grafted onto a polymer such cotton cellulose, in the presence of a monomeric unit such as acrylonitrile. Thereafter, the hydantoin units in the grafted copolymers are readily converted to N-halamine structures on exposure to a halogenated material (e.g., chlorine bleach). The N-halamine derivatives of the corresponding grafted samples exhibit potent antibacterial properties against microorganisms e.g., *Escherichia coli*. Moreover, these antibacterial properties are durable and regenerable.

These and other features and advantages will become more apparent when read with the accompanying figures and detailed description that follows.

DEFINITIONS

As used herein "ADMH" means 3-allyl-5,5-dimethylhydantoin.

As used herein "AIBN" means 2,2'-azobisisobutyronitrile.

As used herein "AN" means acrylonitrile.

As used herein "BADD" means 7,8-benzo-1,3-diazasprio[4.5]decane-2,4-dione.

As used herein "BADDD" means 7,8-benzo-3-allyl-1,3-diazaspiro[4.5]decane-2,4-dione.

As used herein "DMH" means 5,5-dimethylhydantoin.

As used herein "MMA" means methyl methacrylate.

As used herein "PPS" means potassium persulfate.

As used herein "VAC" means vinyl acetate.

As used herein, the term "alkyl" denotes branched or unbranched hydrocarbon chains, preferably having about 1 to about 8 carbons, such as, methyl, ethyl, n-propyl, isopropyl, n-butyl, sec-butyl, iso-butyl, tert-butyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

The term "alkylene" refers to a divalent alkyl group as defined above, such as methylene (—$CH_2$—), propylene (—$CH_2CH_2CH_2$—), chloroethylene (—$CHClCH_2$—), 2-thiobutene —$CH_2CH(SH)CH_2CH_2$, 1-bromo-3-hydroxyl-4-methylpentene (—$CHBrCH_2CH(OH)CH(CH_3)CH_2$—), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "alkoxy" denotes —OR—, wherein R is alkyl.

The term "amido" denotes an amide linkage: —C(O)NHR (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "alkylcarbonyl" denote an alkyl group as defined above subsituted with a C(O) group, for example, $CH_3C(O)$—, $CH_3CH_2C(O)$—, etc.

The term "alkylcarboxyl" denote an alkyl group as defined above subsituted with a C(O)O group, for example, $CH_3C(O)O$—, $CH_3CH_2C(O)O$—, etc.

The term "carbocycle" means a cyclic hydrocarbon chain having about 5 to about 8 ring carbons such as cyclopentyl, cylcohexyl, etc. These groups can be optionally substituted with one or more functional groups as defined under "alkyl" above.

The term "halogen" includes chlorine, fluorine, bromine, iodine and mixtures thereof The term "heterocycle" means a straight chain or ring system that may contain from zero to four heteroatoms selected from N, O, and S, wherein the nitrogen and sulfur atoms are optionally oxidized, and the nitrogen atom(s) are optionally quaternized. Non-limiting examples of heterocycle groups include 1-pyrrolyl, 2-pyrrolyl 3-pyrrolyl, 3-pyrazolyl, 2-imidazolyl, 4-imidazolyl, pryrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, etc. These groups can be optionally substituted with one or more functional groups as defined under "alkyl" above.

The terms "antimicrobial," "microbicidal," or "biocidal" as used herein, refer to the ability to kill at least some types of microorganisms, or to inhibit the growth or reproduction of at least some types of microorganisms. The polymers prepared in accordance with the present invention have microbicidal activity (antimicrobial) against a broad spectrum of pathogenic microorganisms. For example, if the polymer is grafted to a textile, the textiles have microbicidal activity against representative gram-positive (such as *Staphylococcus aureus*) and gram-negative bacteria (such as *Escherichia coli*). Moreover, the microbicidal activity of such textiles is readily regenerable.

DETAILED DESCRIPTION OF THE INVENTION AND PREFERRED EMBODIMENTS

In one embodiment, the present invention provides heterocyclic vinylic compounds that can be used to form microbiocidal polymers. In other aspects, the polymers thus made can be grafted onto textiles, fabrics and polymers. The polymers are readily converted to N-halamine structures on exposure to a halogen source such as commercially available chlorine bleach. The N-halamine derivatives of the corresponding grafted samples exhibit potent antibacterial properties against microorganisms such as *Escherichia coli*, and these properties are durable and regenerable.

As such, in certain aspects, the present invention provides a compound having the formula

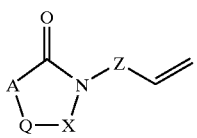

Figure 1:
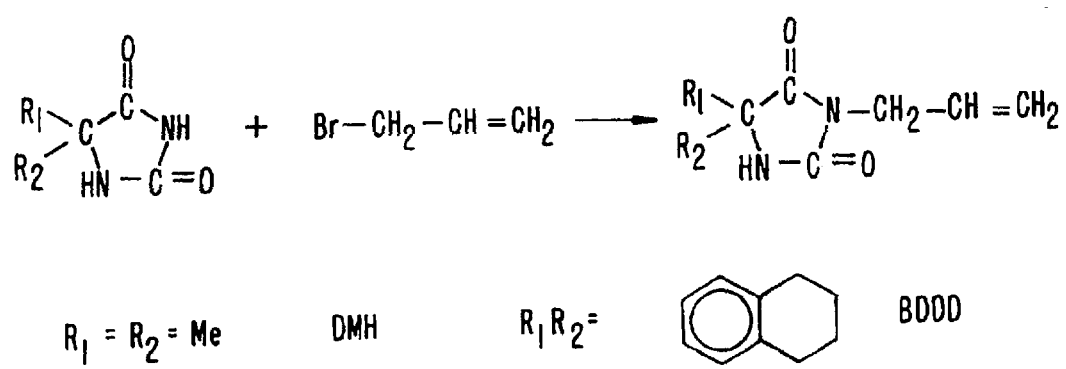
FIG. 1 illustrates a representative synthesis scheme for compounds of the present invention.

I wherein A, Q, X, Z, $R^1$, $R^2$, $R^3$, $R^4$, $R^5$, $R^6$, $R^7$, R8, and $R^9$ have been defined above. With reference to FIG. 1 an illustrative example of the synthesis of a compound of Formula I is set forth. FIG. 1 is merely an example that should not limit the scope of the claims herein. One of ordinary skill in the art will recognize many other variations, alternatives, and modifications. As shown therein, to a solution of DMH in water containing KOH was added allyl bromide in methanol. The solution was stirred at elevated temperature. Thereafter, the solution was cooled and dried under reduced pressure at room temperature to produce a compound of Formula I.

Suitable heterocyclic amine reagents useful in the synthesis reaction illustrated in FIG. 1, include, but are not limited to, 6,6-dimethyl-1,3,5-triazine-2,4-dione, 4,4,5,5-tetramethyl-1,3-imidazolidin-2-one, and 5,5-dimethylhydantoin, and mixtures thereof. Compounds of Formula I wherein Z is $CH_2$ that generates a heterocyclic allylic amine are preferred. Certain preferred compounds of Formula I are set forth in Table 1.

TABLE 1

| Compound | A | Q | X | Z |
|---|---|---|---|---|
| 1 | NH | $CR^3 R^4$<br>$R^3$ is $CH_3$<br>$R^4$ is 4-methylbenzyl | C(O) | $CH_2$ |
| 2 | NH | $CR^3 R^4$<br>$R^3$ and $R^4$ join to form cyclopentyl | C(O) | $CH_2$ |
| 3 | NH | C(O) | $CR^6 R^7$<br>$R^6$ is $CH_3$<br>$R^7$ is $CH_3$ | $CH_2$ |
| 4 | NH | $CR^3 R^4$<br>$R^3$ is $CH_3$<br>$R^4$ is $CH_3$ | $CR^6 R^7$<br>$R^6$ is $CH_3$<br>$R^7$ is $CH_3$ | $CH_2$ |
| 5 | NH | C(O) | NH C(O) | $CH_2$ |
| 6 | $CR^1 R^2$<br>$R^1$ is $CH_3$<br>$R^2$ is $CH_3$ | NH | C(O) | $CH_2$ |
| 7 | Substituted Cyclohexyl | NH | C(O) | $CH_2$ |
| 8 | NH | C(O) | C(O)-N-allyl | $CH_2$ |

Once generated, the compounds of Formula I are used to generate polymers such as copolymers. Unlike other reported vinylic monomers, in which the copolymerization with other monomers is sluggish, the compounds of Formula I, such as ADMH and BADDD, can be copolymerized with most acrylic, substituted-acrylic and vinyl monomers. The reaction proceeds smoothly under ordinary conditions with a very satisfactory conversion. In certain aspects, about 5 mole % to about 100 mole % of compounds of Formula I can be copolymerized with other monomers, more preferably about 5 mole % to about 50 mole %.

In certain aspects, the compounds of Formula I alone, or together, can be polymerized with at least one other existing vinyl monomer, with or without the addition of free radical initiators, in bulk, aqueous solution or suspension, organic solvents, or emulsions, The resultant polymers can thereafter be used as plastics, rubbers, polymeric materials, paints, surface coatings, adhesives, etc, in the form of bulk, films/membranes, powder, solutions, gels, etc.

As such, in another embodiment, the present invention provides a polymer comprising a mixture of monomer units having the formula

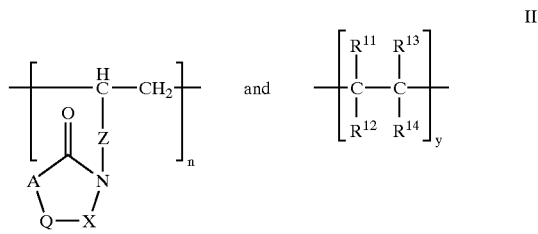

II wherein A, Q, X, Z, $R^1$, $R^2$, $R^3$, $R^4$, $R^5$, $R^6$, $R^7$, $R^8$, $R^9$, $R^{10}$, $R^{11}R^{12}$, $R^{13}$, $R^{14}$, "n" an "y" have been defined above. In this embodiment, a compound of Formula I and a vinyl monomer, such as an acrylic monomer, a monofunctional vinyl monomer, a polyfunctional vinyl monomer and mixtures thereof, are reacted together to form copolymers.

Examples of such vinyl monomers include, but are not limited to, acrylonitrile, styrene, acrylamide, methacrylamide, methyl methacrylate, ethylene, propylene, butylenes, butadienes and other alkenes and dienes. The copolymers thus formed have a least one dimmeric unit wherein "n" is 1and "y" is 1.

In certain embodiments, each of end groups in the polymers are hydrogen. The polymers of the present invention comprise at least one dimmeric unit of Formula II, wherein n is 1 and y is 1. In certain aspects, the units of Formula II are grafted onto existing polymers. The polymers comprise varying amounts of units of "n" and "y", i.e., the number of "n" and "y" units can be random. For example, the polymer can comprise about 10 "n" units followed by about 20 "y" units or visa versa. All combinations and variations of "n" and "y" are encompassed and contemplated by the present invention.

In certain aspects, the present invention provides a polymer comprising a polymeric unit having the formula:

In yet another embodiment, the present invention provides a polymer comprising a polymeric unit of the formula:

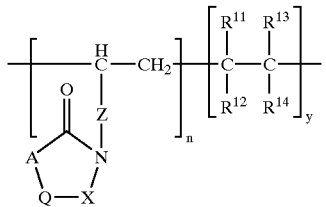

III wherein A, Q, X, Z, $R^1$, $R^2$, $R^3$, $R^4$, $R^5$, $R^6$, $R^7$, $R^8$, $R^9$, $R^{10}$, $R^{11}R^{12}$, $R^{13}$, $R^{14}$, "n" and "y" have been defined above. In this embodiment. The polymer comprises a least one unit having a dimmer wherein "n" is 1 and "y" is 1.

As merely as an example, that should not limit the scope of the claims herein, copolymerization of compounds of Formula I wherein Z is $CH_2$ e.g., ADMH or BADDD, will be illustrated. One of ordinary skill in the art will recognize many other variations, alternatives, and modifications. In certain aspects, the ease of copolymerization is attributable to the an imide structure generated during polymerization. Surprisingly, the polymerization reaction of the present invention proceeds without termination of the growing polymer chain or termination of the kinetic chain as in prior art systems. (see, Schildknecht, C. E., *Allyl Compounds and Their Polymers*, John Wiley & Sons, New York, 1973, p 30; Shigetomi, Y., el al., *J. Polym. Sci., part A, Polym. Chem.*, 28:3317 (1990)). Without being bound by any particular theory, it is believed that the strong electron-withdrawing ability of the imide group lowers the electron density of the allylic carbon, and thus, the termination steps involving the abstraction of the allylic hydrogen in allyl copolymerizations is retarded. As a result, degradative chain transfer decreases, and satisfactory copolymerization takes place.

Although it is possible to prepare homopolymers of the compounds of Formula I employing the methods described herein, "autoinhibition" of allylic structures may occur. However, homopolymers comprising "n" unit polymers are an aspect of the present invention. Once formed, the allylic radical is very stable, with the result that degradative chain transfer competes exceptionally well with normal propagation, and the polymer chains are terminated after the addition of only a few monomer units (see, Bartlett, P. D. et al., *J. Am. Chem. Soc.*, 75:91 (1953); Schildknecht, C. E., *Allyl Compounds and Their Polymers*, John Wiley & Sons, New York, 1973, p 30.)). This characteristic is not necessarily a disadvantage. For example, less homopolymerization ensures an excellent yield in the monomer synthesis process described above, as well as good storage stability and a prolonged shelf-life.

Once formed, the polymers can be made biocidal by reacting the corresponding unhalogenated polymers, with a halogen source. Suitable halogenating agents such as calcium hypochlorite, sodium hypochlorite (e.g. CLOROX®), N-chlorosuccinimide, N-bromosuccinimide, sodium dichloroisocyanurate, trichloroisocyanuric acid, tertiary butyl hypochlorite, N-chloroacetamide, N-chloramines, N-bromamines, etc., can be used.

The halogenation of the unhalogenated polymers can be accomplished in aqueous media or in mixtures of water with common inert organic solvents such as methylene chloride, chloroform, and carbon tetrachloride, or in inert organic solvents themselves, at room temperature. Those of skill in the art will know of other solvents or solvent mixtures suitable for use in the present invention. In certain instances, the unhalogenated polymers can be a previously-utilized cyclic N-halamine polymer that needs to be regenerated due to inactivation of the N-halamine moieties. As used herein, "halogenating" or "halogenated" polymers refers to partially as well as fully halogenated. Preferred halogens are chlorine and bromine.

Figure 2:
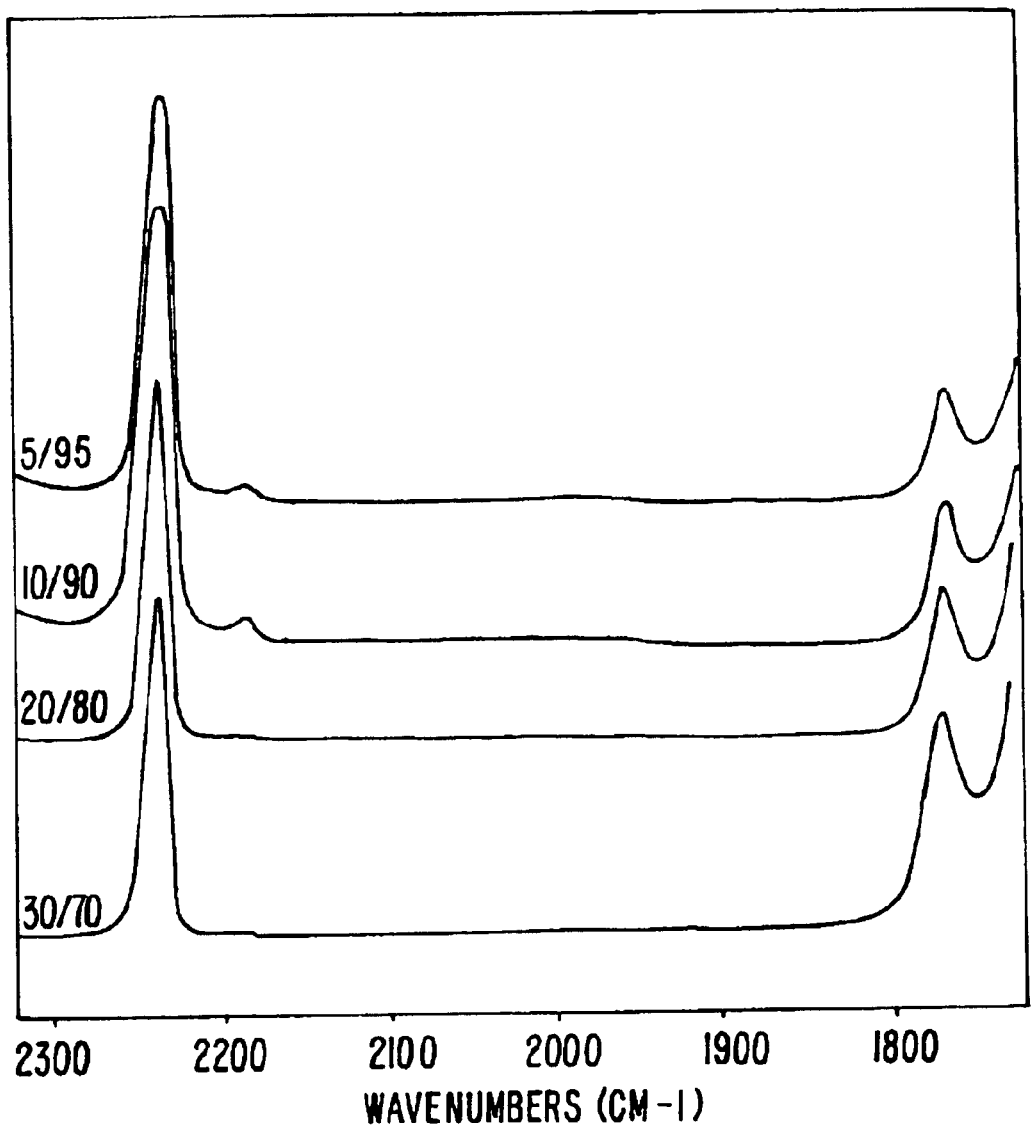
FIG. 2 illustrates a FT-IR spectrum FT-IR spectra of PAN and ADMH physical mixtures of different ADMH/PAN weight ratio in the range of 1725 to 2325 $cm^{-1}$.

Once formed, it is possible to determine copolymer contents from the FT-IR spectra of the polymers (see, for example, Nyquist, R. A., *Appl. Spectrosc.*, 41, 797 (1987); Liu, M. X. et al., *Appl. Spectrosc.*, 50:349 (1996)). With reference to FIG. 2, the FT-IR spectra of PAN and ADMH physical mixture films cast from DMF solution are shown in the range of 1725 to 2330 $cm^{-1}$. With an increase in ADMH content, the intensity of the 1770 $cm^{-1}$ band also increases, while that of the 2243 $cm^{-1}$ band decreases.

Figure 3:
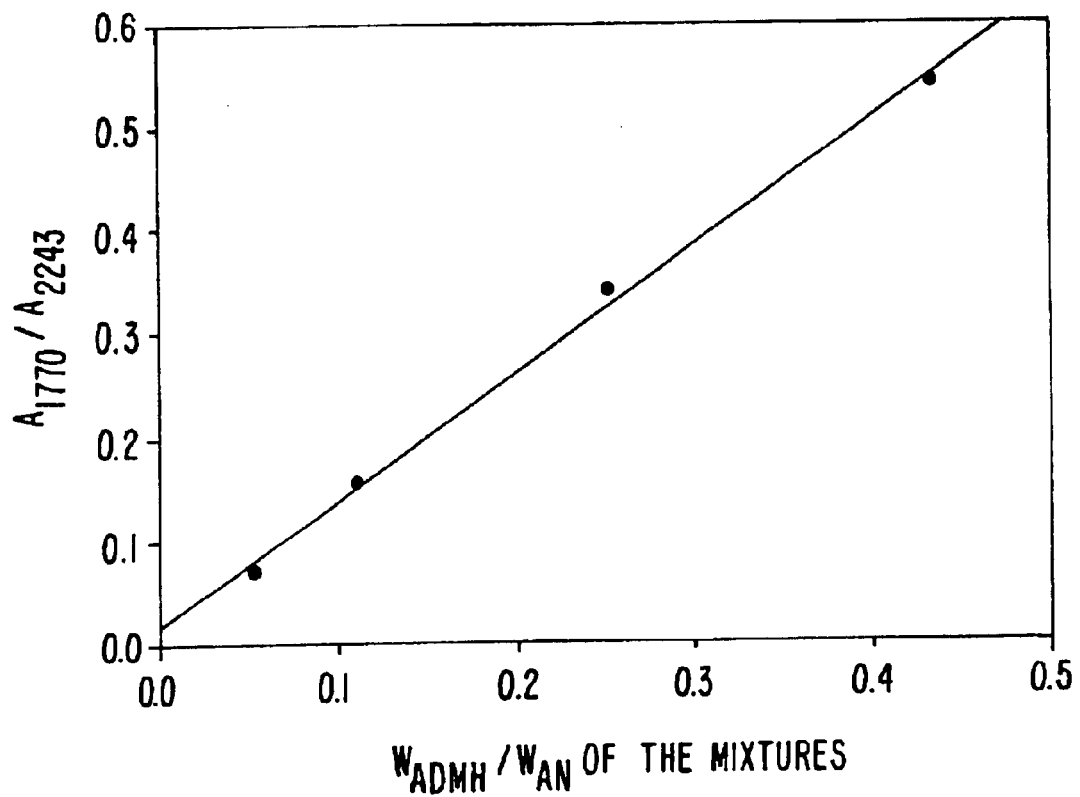
FIG. 3 illustrates a representative method of determining copolymerization of the present invention.

FIG. 3 shows the plot of $A_{1770}/A_{2243}$ vs. $W_{ADMH}/W_{AN}$, wherein $A_{1770}$ and $A_{2243}$ represents the area of the 1770, 2243 $cm^{-1}$ bands, and $W_{ADMH}$, $W_{AN}$, the weight of ADMH and AN in the physical mixtures, respectively. A linear relationship is obtained and the slope is determined to be 0.74. Thus, the weight content of ADMH units in an "An-co-ADMHW" copolymer is calculated to be 3.4%. Similarly, the hydantoin contents of other copolymers were obtained, as shown in Table 2. In the copolymers, the hydantoin structure contents are all below 5% wt (the original monomer ratio), and the BADDD contents are usually lower than ADMH except in the case of "MMA-co-BADDD", where bulk copolymerization was employed.

In certain other embodiments, the present invention provides a method for making a polymer, comprising:

admixing a compound having the formula

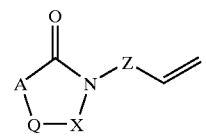

I wherein A, Q, X, Z, $R^1$, $R^2$, $R^3$, $R^4$, $R^5$, $R^6$, $R^7$, R8, and $R^9$ have been defined above, with a with a vinyl monomer in a reaction mixture thereby making the polymer. Vinyl monomers suitable for use in the present invention include, but are not limited to, an acrylic monomer, a monofunctional vinyl monomer, a polyfunctional vinyl monomer and mixtures thereof The polymerization reaction proceeds with a compound of Formula I and at least one other existing vinyl monomer, optionally in the presence of a free radical initiator. The reaction can take place in bulk, an aqueous solution or a suspension, or an organic solvent, or emulsion.

In another embodiment, the present invention provides a method for chemically modifying a polymer, comprising: admixing the polymer in a reaction mixture with a compound having the formula

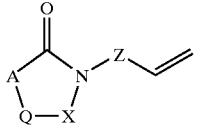

I wherein A, Q, X, Z, $R^1$, $R^2$, $R^3$, $R^4$, $R^5$, $R^6$, $R^7$, $R^8$, and $R^9$ have been defined above, with a with a vinyl monomer in a reaction mixture thereby chemically modifying the polymer. As used herein "chemical modification" includes grafting the monomers alone or as a copolymer onto existing natural or synthetic polymers in the presence of at least one other existing vinyl monomer. The polymerization and chemical modification reactions can be initiated by thermal or radiation method, or the combinations thereof, optionally in the presence of initiators. The resultant grafted polymers can be used as plastics, rubbers, polymeric materials, paints, surface coatings, adhesives, etc., in the form of bulk, films/membranes, powder, solutions, gels, etc.

For example, a hydantoin-containing monomer such as 3-allyl-5,5-dimethylhydantoin (ADMH), is grafted onto a textile in the presence of a vinyl monomeric unit such as acrylonitrile (AN). In this aspect, a compound of Formula I in the grafted copolymers are readily converted to N-halamine structures on exposure to a halogenated material, such as commercially available chlorine bleach. The exposure to a halogenated source generates a N-halamine, and these structures are biocidal. Advantageously, compounds of Formula I can readily be grafted onto other polymers such as fabrics, in the presence of mono or polyfunctional acrylic and vinyl monomers.

Various polymers can be chemically modified using the methods of the present invention. Polymers suitable for use in the present invention include, but are not limited to, a plastic, a rubber, a textile material, a paint, a surface coating, an adhesives, cellulose, a polyester, wood pulp, paper and a polyester/cellulose blend. The polymeric materials suitable for the present invention include, but are not limited to, naturally occurring fibers from plants, such as cellulose, cotton, linin, hemp, jute and ramie. They include polymers from animals, based upon proteins and include, but are not limited to, wool, mohair, vicuna and silk. Textiles also include manufactured fibers based upon natural organic polymers such as, rayon, lyocell, acetate, triacetate and azlon. Textiles suitable for use in the present invention include synthetic organic polymers which include, but are not limited to, acrylic, aramid, nylon, olefin, polyester, spandex, vinyon, vinyl and graphite. Textiles also include inorganic substances such as glass, metallic and ceramic.

Various textiles are preferred to practice the invention. These include, but are not limited to, a fiber, a yarn or a natural or synthetic fabric. Various fabrics include, but are not limited to, a nylon fabric, a polyester, an acrylic fabric, NOMEX®, a triacetate, an acetate, a cotton, a wool and mixtures thereof NOMEX is made of an aromatic polyamide material and is available from DuPont (Wilmington, Del.). NOMEX is used in fire fighting equipment.

The polymeric plastics suitable for the present invention include thermoplastic or thermosetting resins. The thermoplastics include, but are not limited to, polyethylene, polypropylene, polystyrene, and polyvinylchloride. Thermoplastics also include, polyamideimide, polyethersulfone, polyarylsulfone, polyetherimide, polyarylate, polysulfone, polycarbonate and polystyrene. Additional thermoplastics include, but are not limited to, polyetherketone, polyetheretherketone, polytetrafluoroethylene, nylon-6,6, nylon-6,12, nylon-11, nylon-12, acetal resin, polypropylene, and high and low density polyethylene.

The polymerization and chemical modification reactions can proceed by various polymerization techniques well known by those of skill in the art. For example, a free radical initiation method, a photoinitiated method or thermal initiated method are all suitable methods. For example, one can dissolve a compound of Formula I in absolute ethanol or other suitable solvent and react this solution, at the boiling point for the solvent, with azobisisobutyronitrile (AIBN) under nitrogen atmosphere to produce the unhalogenated polymer.

Alternatively, the compounds of Formula I can be copolymerized with a vinyl monomers by a free radical initiation method, such as by dissolving all desired monomers in N,N-dimethylacetamide or other suitable solvent and adding, under nitrogen atmosphere, azobisisobutyronitrile, and allowing the mixture to react, at the boiling point temperature for the solvent, under nitrogen atmosphere to produce the copolymer. For example, other monomer types that can be copolymerized with a compound of Formula I can include acrylonitrile, styrene, methacrylamide, methylmethacrylate, ethylene, propylene, butylenes, butadienes and other alkenes and dienes. The resulting unhalogenated polymers or copolymers can then be halogenated, such as with free chlorine and bromine sources, as described herein. Additionally, the compound of Formula I can be halogenated and thereafter polymerized.

Figure 4:
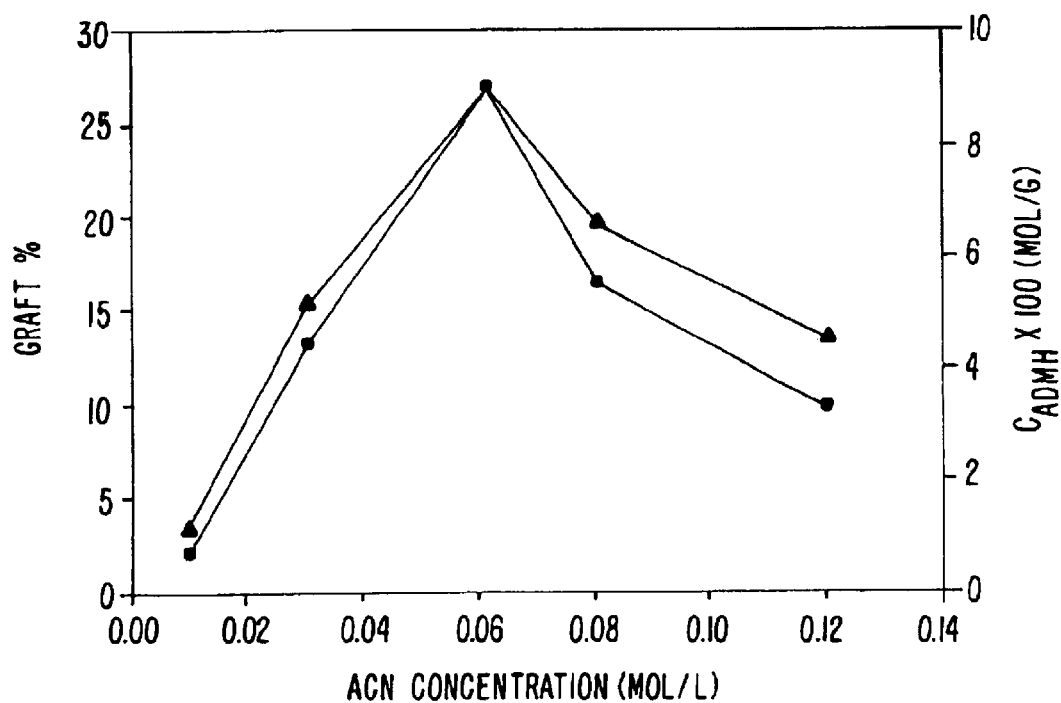
FIG. 4 illustrates a representative embodiment of varying free-radical initiator on polymerization yields of the present invention. Effect of ACN concentration on: ▲ percentage graft, and ■ $C_{ADMH}$ (Total monomer concentration: 5 wt %; ADMH molar fraction: 20 mol %; T=45° C. and t=180 min).

Various parameters of the polymerization and chemical modifications were examined to optimize the reactions. These parameters, such as concentration of radical initiator, will be illustrated with a specific example. However, this is merely an example that should not limit the scope of the claims herein. One of ordinary skill in the art will recognize many other variations, alternatives, and modifications. In certain instances, the concentration of free radical initiator can have an effect on the polymerization reaction. For example, with reference to FIG. 4, the effect of varying the concentration of ACN on the percentage graft yield and $C_{ADMH}$ is presented. ($C_{ADMH}$ is the mole content of the ADMH unit in the grafted polymer). As shown therein, the percentage of graft obtained and $C_{ADMH}$ increase and thereafter decrease after an optimum value of 0.06 mol/L. Without being bound by any particular theory, it is believed that as the concentration of ACN increases, a large number of cotton macroradicals form, thereby increasing the graft yield and $C_{ADMH}$. However, when the concentration of ACN is higher than 0.06 mol/L, further increase in initiator concentration may bring about the following effects: (1) abundant free radicals, as well as PAN homopolymer and/or AN/ADMH copolymer macroradicals are formed in the solution that might terminate the growing chain; (2) the free radicals formed on the main chain of cotton cellulose might be oxidized and thus terminate the reactive sites; and (3) the graft copolymerization, homopolymerization of AN, and the copolymerization of ADMH/AN in such a system is a matter "competition", which depends on the direct attack of free radicals to cotton or to monomers. In certain instances, the net result is a higher concentration of initiator results in the production of more free radicals, and thus more homopolymer/copolymer macroradicals, thereby reducing the graft yield, as well as the ADMH unit content in the grafted samples.

In certain instances, the concentration of the compound of Formula I has an effect on the polymerization reaction. For example, the graft copolymerization of ADMH/AN monomer mixtures onto cotton was investigated by varying the ADMH molar fraction in the mixtures. In certain instances, the data shows that with increased ADMH content in the monomer mixtures, graft yield decreases. For example, grafting AN alone onto cotton results in a graft yield of 63.8 wt %; however, keeping other conditions constant, when the molar ratio of ADMH in the mixtures is 50%, the graft yield is 3.2 wt % (see, FIG. 5). When the molar content of ADMH was higher than 50%, the monomer mixtures acted as pure ADMH, i.e., extended periods of grafting (12 h) resulted in a graft yield of about 1 wt %. Thus, in certain instances, the presence of ADMH reduces the graft yield of the AN component, which can also be explained by the "autoinhibition" effect of the allylic structure in ADMH. However, "AN" enhances the ADMH graft yield to a considerable extent, showing positive synergism.

Figure 5:
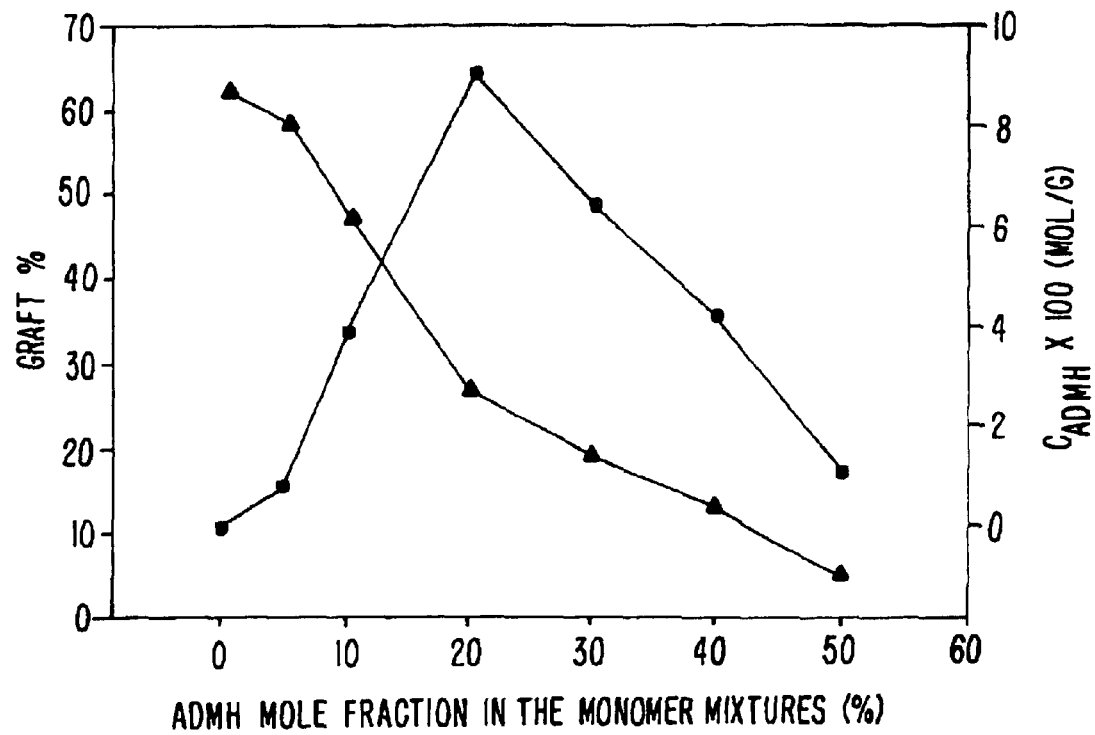
FIG. 5 illustrates an effect of mole fraction in the monomer mixture on graft copolymerization of the present invention. Effect of ADMH mole fraction in the monomer mixtures on: ▲ percentage graft, and ■ $C_{ADMH}$ (Total monomer concentration: 5 wt %; ACN concentration: 0.06 mol/L, T=45° C. and t=180 min).

In other aspects, the ADMH molar content in the monomer mixtures influences the value of $C_{ADMH}$. In certain instances, this value increases with the increase of ADMH molar content up to 20% and then decreases with further increases in the ADMH content, as shown in FIG. 5. Without being bound by any particular theory, this "increase-decrease" trend may be explained by an "equilibrium" between graft yield and $\Phi_{ADMH}$. Increasing the ADMH molar content, causes the total graft yield to decrease, while the content of the ADMH units in the grafted copolymers ($\Phi_{ADMH}$) increases. Thus, at a certain ADMH molar content (about 20%), a maximum value of $C_{ADMH}$ can be observed. For $C_{ADMH}$, the synergistic effect was at its highest when an AN/ADMH mixture containing 20 mol % ADMH was used.

Figure 6:
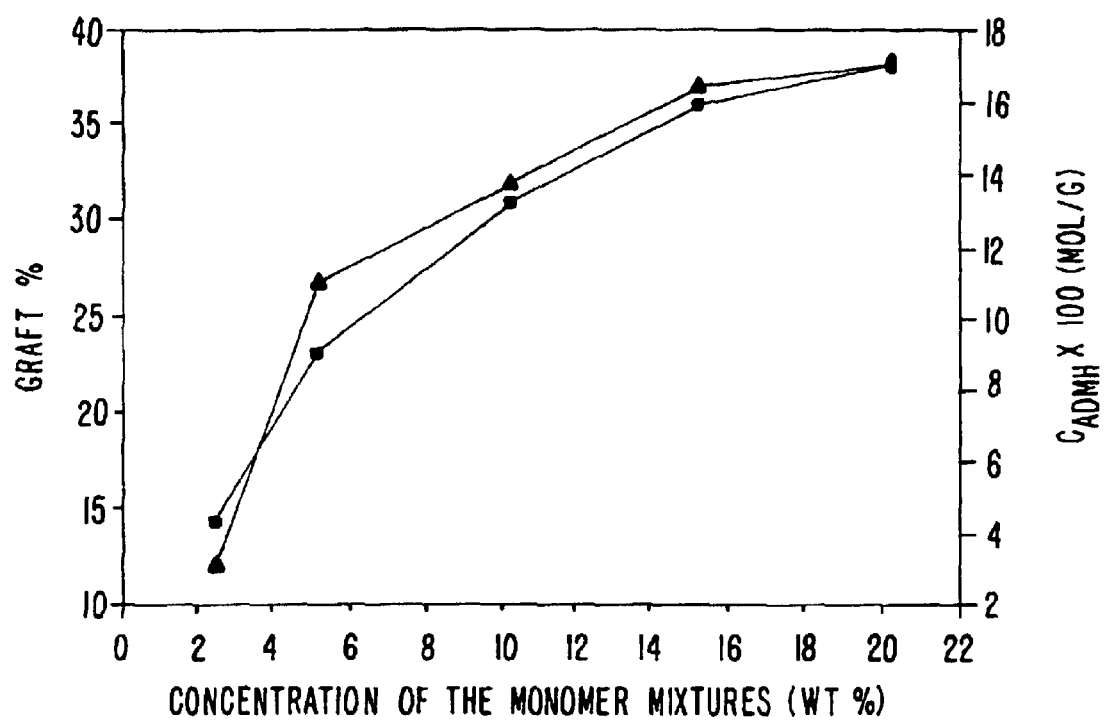
FIG. 6 illustrates an effect of monomer concentration on graft copolymerization of the present invention. Effect of total monomer concentration on: ▲ percentage graft, and ■ $C_{ADMH}$ (ADMH molar fraction: 20 mol %; ACN concentration: 0.06 mol/L, T=45° C. and t=180 min).

FIG. 6 shows the influence of the monomer mixture concentration on graft copolymerization. In certain instances, by increasing the total monomer concentrations, the graft yield and $C_{ADMH}$ gradually increase. In this heterogeneous reaction system, the graft copolymerization largely depends on the diffusion of monomers to cotton samples. As monomer concentrations go up, more and more monomers can reach reactive sites on cotton molecules. Furthermore, increasing monomer concentrations may increase the amount of PAN homopolymer and/or AN/ADMH copolymer in the solution, and consequently, this will result in increased viscosity. This effect hinders termination, particularly through the coupling of growing polymer chains. So, the graft yield and $C_{ADMH}$ increase.

It should be noted that at higher than 5 wt % total monomer concentration, this trend is not very significant. For example, from 5 wt % to 20 wt %, the monomer concentration increases 4 times, but the graft yield only increases 1.4 times, and $C_{ADMH}$, about 2 times.

Figure 7:
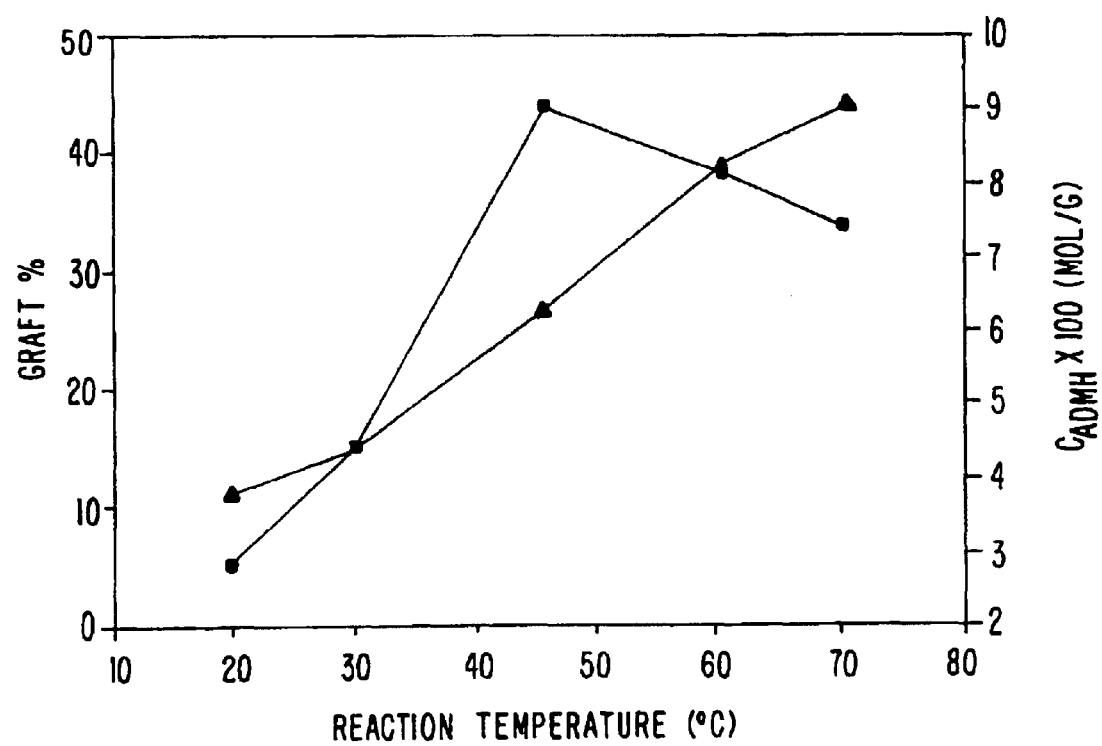
FIG. 7 illustrates an effect of reaction temperature on graft copolymerization of the present invention. Effect of reaction temperature on: ▲ percentage graft, and ■ $C_{ADMH}$ (Total monomer concentration: 5 wt %; ADMH molar fraction: 20 mol %; ACN concentration: 0.06 mol/L, and t=180 min).

In other aspects, the effect of temperature on graft copolymerization was investigated over the range of 20–70° C. With reference to FIG. 7, in certain instances, the percentage graft increases with the increase of temperature. In case of $C_{ADMH}$, it first increases with the increase of temperature up to 45° C., and beyond this limit it decreases.

Without being bound by any particular theory, it is believed that the "increase-decrease" trend of $C_{ADMH}$ is most likely due to the influence of temperature on $\Phi_{ADMH}$: it was found that $\Phi_{ADMH}$ increases with the increase in temperature up to 45° C.; and after this, further increases in temperature decreased $\Phi_{ADMH}$. Consequently, at higher than 45° C., although the percentage graft increases, $C_{ADMH}$, decreases. Without being bound by any particular theory, these findings may suggest that compared with ADMH, polymerization of AN is favored at higher-temperatures. Moreover, at higher temperatures (higher than 45° C.), some PAN homopolymer, instead of AN/ADMH copolymer, may be grafted onto cotton fibers.

Figure 8:
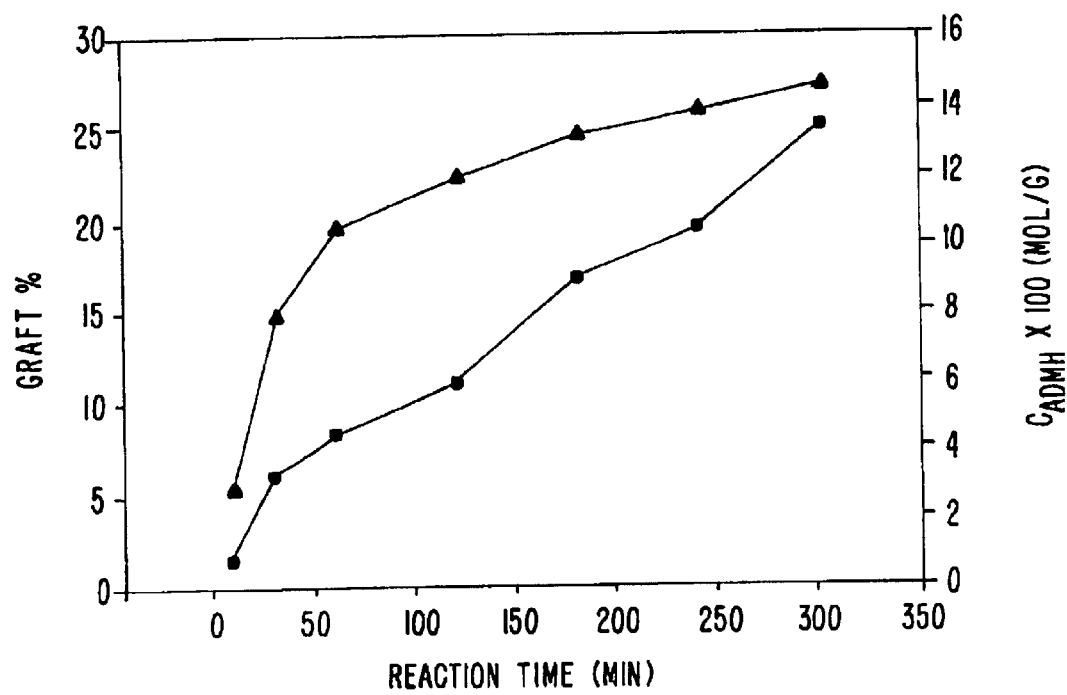
FIG. 8 illustrates an effect of reaction time on graft copolymerization of the present invention. Effect of reaction time on: ▲ percentage graft, and ■ $C_{ADMH}$ (Total monomer concentration: 5 wt %; ADME molar fraction: 20 mol %; ACN concentration: 0.06 mol/L, and T=45° C.).

In certain aspects, reaction time influences graft copolymerization. For example, with reference to FIG. 8 with longer reaction time, both percentage graft and $C_{ADMH}$ increase, but to different degree. For example, from 30 to 300 min, the percentage graft increases only 1.7 times, but for $C_{ADMH}$, the increase is 4.3 times. This means that with longer reaction times, $\Phi_{ADMH}$ and $C_{ADMH}$ increase more quickly than the percentage graft. The reactivity of AN is higher than that of ADMH, and thus, AN preferentially enters the copolymer. As a result, there is a drift in the co-monomer composition toward ADMH as the reaction time is extended, and the percentage graft increases more slowly than $C_{ADMH}$.

Numerous applications for the biocidal polymers of the present invention exist. For instance, the biocidal polymers can provide biocidal protective clothing to personnel in the medical area as well as in the related healthcare and hygiene are. The regenerable and reusable biocidal materials can replace currently used disposable, nonwoven fabrics as medical textiles, thereby significantly reducing hospital maintenance costs and disposal fees. The microbicidal properties of the polymers of the present invention can be advantageously used for women's wear, underwear, socks, and other hygienic purposes. In addition, the microbicidal properties can be imparted to carpeting materials to create odor-free and germ-free carpets. Moreover, all germ-free environments, such as required in biotechnology and pharmaceutical industry, would benefit from the use of the microbicidal textiles of the present invention to prevent any contamination from air, liquid, and solid media.

The biocidal polymer are effective against all microorganisms. Such microorganisms include, for example, bacteria, protozoa, fungi, viruses and algae. Moreover, the biocidal polymers described herein can be employed in a variety of disinfecting applications, such as water purification. They will be of importance in controlling microbiological contamination or growth of undesirable organisms in the medical and food industries. In addition, they can be used as preservatives and preventatives against microbiological contamination in paints, coatings, and on surfaces.

EXAMPLES

The following examples are offered to illustrate, but not to limit the claimed invention.

a) Materials

Bleached desized cotton print cloth #400 (Testfabrics Inc.) was used throughout this study. 5,5-dimethylhydantoin (DMH, Aldrich), ammonium cerium (IV) nitrate (Acros, ACN) and allyl bromide (Acros) were used without further purification. AN (Acros) was distilled twice before use. 7,8-Benzo-1,3-diazaspiro[4.5]decane-2,4-dione (BDDD, Aldrich) and allyl bromide (Acros) were used without further purification. AN, VAC, and MMA were distilled twice under reduced pressure. 2,2'-Azobisisobutyronitrile (AIBN) and potassium persulfate (PPS) was recrystallized from EtOH and distilled water, respectively.

b) Instruments

FT-IR spectra were taken on a Nicolet Magana IR-560 spectrometer using KBr pellets. The samples were made to be thin enough to ensure that the Beer-Lambert law was fulfilled. $^1$H-NMR spectra were recorded on a GE NMR QD-300 spectrometer. The DSC study of the samples was performed using a Shimadzu DSC-50 instrument at a heating rate of 20° C./min under $N_2$ atmosphere.

Example 1

This example illustrates the synthesis of ADMH and BADDD.

With reference FIG. 1, a solution of 6.4 g (0.05 mole) of DMH in 25 mL $H_2O$ containing 2.8 g (0.05 mole) of KOH was combined with a solution of 4.4 mL (0.05 mole) allyl bromide in 10 mL of methanol. The solution was stirred at 60° C. for 2 h, cooled, and dried under reduced pressure at room temperature. The solid was recrystallized from petroleum ether, yielding, 7.7 g (92%) of ADMH; m.p., 74–75°

C. $^1$H-NMR (DMSO-d 6, δ): 1.29(6H, s, CH$_3$), 3.94(2H, d, N—CH$_2$), 4.99–5.12(1H, m, =CH), 5.73–5.86(2H, m, =CH$_2$), 8.33(1H, s, NH).

BADDD was prepared in a similar fashion and recrystallized from isopropyl alcohol, with a yield of 68% and m.p., 160–161° C. $^1$H-NMR (DMSO-d$_6$, δ): 1.83–2.08(2H, m, CH$_2$), 2.77–2.96(2H, m, CH$_2$), 3.08–3.34(2H, m, CH$_2$), 3.98–3.99(2H, d, N—CH$_2$), 5.04–5.14(1H, m, =CH), 5.76–5.89(2H, m, =CH$_2$), 7.14(4H, m, benzene ring), 8.69 (1H, s, NH).

Figure 9:
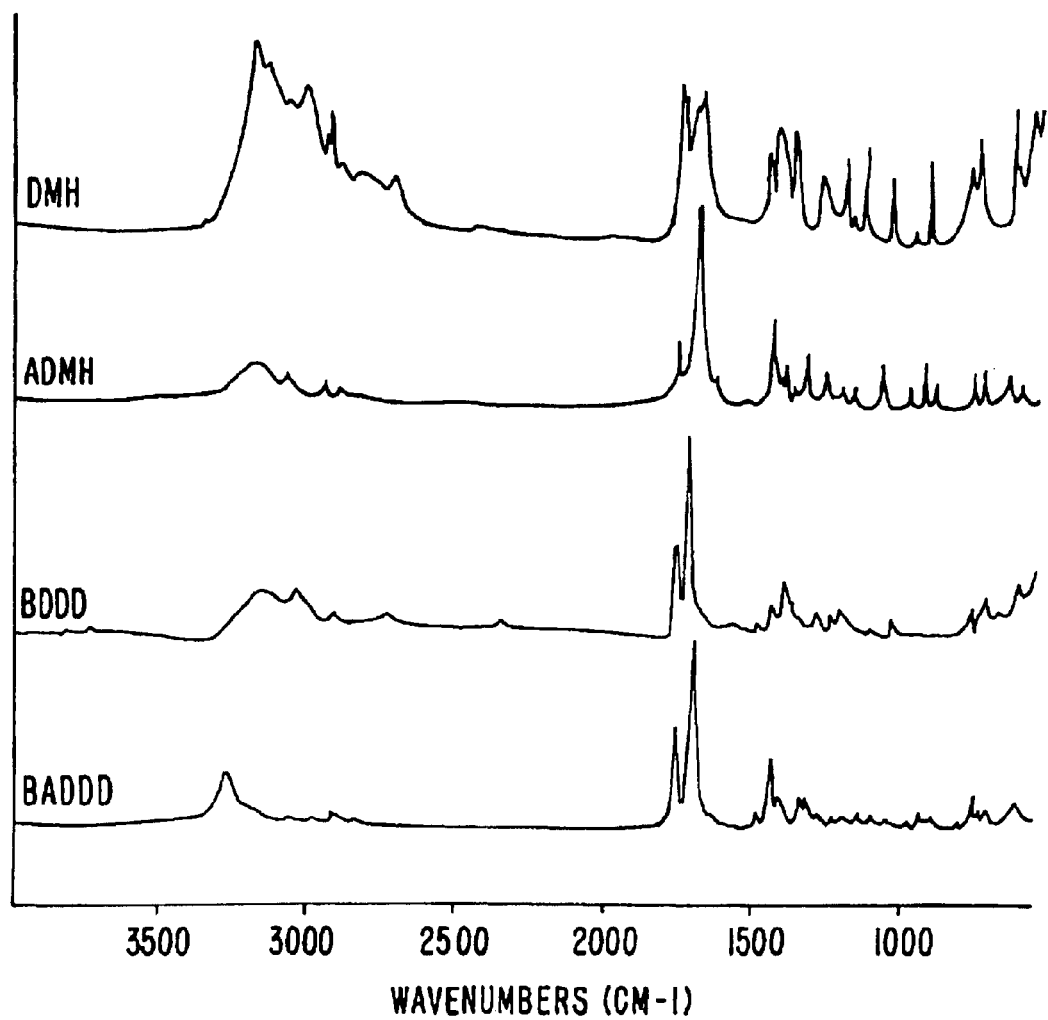
FIG. 9 illustrates a FT-IR spectrum of an embodiment of the present invention.

Both ADMH and BADDD showed significant differences from their corresponding parent chemicals in FT-IR and $^1$H-NMR spectra. FIG. 9 shows the FT-IR spectra of DMH, ADMH, BDDD and BADDD. It can be seen clearly that unlike DMH which shows two absorption bands in the region of 3000~3500 cm$^{-1}$, ADMH has only one band in this region. Furthermore, the C=O stretching band shifts from 1727 cm$^{-1}$ in DMH to 1710 cm$^{-1}$ in ADMH. Similar changes from BDDD to BADDD can also be found in their FT-IR spectra. With regard to the NMR spectra, ADMH shows characteristic peaks at 3.94(2H, d, N—CH$_2$), 4.99–5.12(1H, m, =CH), and 5.73–5.86(2H, m, =CH$_2$), indicative of the allylic structure. Furthermore, DMH shows two peaks in the region of 7.8~11.0, corresponding to the N-1 and N-3 protons, respectively (see, Ware, E. et al., *Chem. Rev.*, 46:403 (1950)), but in the NMR spectrum of ADMH, only one band around 8.5 is observed. Similar changes in the NMR spectra from BDDD to BADDD can also be detected. All these findings suggest typical N-3 substitutions of hydantoins.

Example 2

This example illustrates the synthesis of copolymers using ADMH and BADDD.

Synthesis conditions for the copolymers are summarized in Table 2. About 5 wt % of the two hydantoin-containing monomers was copolymerized with other monomers separately, in order to obtain desired antimicrobial properties without causing deterioration of the original properties of the polymers. AN, MMA and VAC homopolymers were also synthesized using the same conditions as the corresponding copolymers.

centered at 1770 at 1710 cm$^1$, assigned to the amide and imide band of the hydantoin structure respectively, can also be observed. All other copolymers also show these characteristic bands of the hydantoin structures.

The copolymers were characterized by $^1$H-NMR studies. The NMR spectrum of AN-co-ADMH at the copolymerization ratio of 1/6(W$_{ADMH}$/W$_{AN}$) shows characteristic peaks of ADMH at 1.29 (CH$_3$) and 8.5(NH, weak). Furthermore, there are no peaks in the region of 4.99–5.12 and 5.73–5.86, indicating the sample is a polymer, not a mixture of monomers.

The DSC results of PAN, AN-co-ADMH and AN-co-BADDD show a striking feature in the appearance of a sharp endotherm peak at 2800° C. in that of AN-co-BADDD, indicating the melting point of the polymer. It has been widely accepted that PAN has a "semi-crystalline" structure and because of the strong dipole-dipole interaction between CN groups, instead of the melting point, one can only observe the decomposition of the polymer in ordinary thermal studies The existence of a T$_m$ in AN-co-BADDD is very likely, due to the large side groups of BADDD, i.e., not all of the AN units can pack favorably. Consequently, "physical cross-linking" due to dipole-dipole interactions between CN groups is actually diluted, resulting in a detectable T$_m$. In case of AN-co-ADMH, although the ADMH content is higher than that of BADDD in AN-co-BADDD, the side groups of ADMH are much smaller, and little difference between the DSC curves of AN-co-ADMH and PAN can be observed.

Example 3

This example illustrates the antibacterial assessment of copolymers synthesized in Example 2.

The antibacterial properties of VAC-co-ADMH and VAC-co-BADDD were explored. Polymer films were cast from acetone solution. The films (about 0.5 mm thick) were cut into small pieces (about 2 cm$^2$), and then treated with 20 mL 1% CLOROX regular bleach at 40° C. for 1.5 h, then thoroughly washed with distilled water, and dried under reduced pressure to remove free chlorine. 10 μL of an aqueous solution containing 10$^5$–10$^6$ colony forming units (CFU)/mL of *Escherichia coli* were placed onto the surface

TABLE 2

Synthesis Conditions and Some Properties of the Copolymers

|  | AN-co-ADMH | AN-co-BADDD | MMA-co-ADMH | MMA-co-BADDD | VAC-co-ADMH | VAC-BADDD |
|---|---|---|---|---|---|---|
| M1 | ADMH | BADDD | ADMH | BADDD | ADMH | BADDD |
| M2 | AN | AN | MMA | MMA | VAC | VAC |
| M1/M2 (wt) | 1/19 | 1/19 | 1/19 | 1/19 | 1/19 | 1/19 |
| Initiator (M) | PPS | AIBN | PPS | AIBN | AIBN | AIBN |
| Solvent | H$_2$O | DMF | H$_2$O | None | H$_2$O/CH$_3$OH | H$_2$O/CH$_3$OH |
| Temp. (° C.) | 75 | 72 | 75 | 80 | 68 | 68 |
| Time (h) | 1.5 | 2.0 | 1.0 | 0.5 | 4.5 | 5.0 |
| Conversion | 38% | 63% | 22% | 46% | 54% | 42% |
| [η] (dl/g) | 1.344* | 1.864* | 0.446** | 0.412** | 0.776** | 0.623** |
| +W$_{MI}$ (wt %) | 3.4 | 3.1 | 2.2 | 4.1 | 1.8 | 1.2 |

*Measured in DMF at 25° C.
**Measured in acetone at 25° C.
+W$_{MI}$: ADMH or BADDD. Weight fraction in the copolymers.

The FT-IR spectrum of PAN shows absorption bands at 2243, 1454, 1248 and 1073 cm$^{-1}$, which are attributed to the ν(CN), δ(CH$_2$), γ$_w$(CH), and ν+(0), respectively, in agreement with the literature data (see, Liang, C. Y., et al., *J. Polym. Sci.*, 31:513 (1958)). In the spectrum of AN-co-ADMH, besides the characteristic bands of PAN, two bands of the film. The film was then "sandwiched" using an identical film. After different contact times, the entire "sandwich" was placed into 10 mL of 0.03% sodium thiosulfate aqueous solution. The resultant solution was then vigorously shaken for 5 min. An aliquot of the solution was then serially diluted, and 100 μL of each dilution was plated onto a nutrient agar plate. The same procedure was also applied to the un-halogenated samples as controls. Bacterial colonies on the agar plates were counted after incubation at 37° C. for 48 h.

To study the durability of the antibacterial properties of the films, samples were immersed in 500 mL of distilled water at 45° C. for 60 min, and air dried at room temperature for 24 h. After each wash, the antibacterial properties of the treated samples were examined by the same method mentioned above.

In certain instances, powdered samples were used to study their antibacterial properties. One gram of the powder was treated with 20 mL CLOROX regular bleach (sodium hypochlorite 5.25%) at 40° C. for 1.5 h, washed thoroughly with distilled water, and then dried under reduced pressure to remove free chlorine. The antibacterial properties of the halogenated copolymers were tested according to a modified method reported previously. (see, Worley, S. D. et al., *The Polymeric Materials Encyclopedia,* 1, A-B, p. 550 (1996)). 10 mL of an aqueous solution containing $10^5$–$10^6$ CFU/mL of *Escherichia coli* passed through a column containing about 1 cm length of the corresponding sample powders, using gravity feed. The effluent was collected and the diluted solutions were plated onto nutrient agar plates. Same procedure was also applied to un-halogenated samples as controls. Bacterial colonies on the agar plates were counted after incubation at 37° C. for 24 h.

Example 4

This example further illustrates the antibacterial assessment of copolymers synthesized in Example 2.

After treatment with CLOROX regular bleach, the amide groups of the copolymers are readily transformed into N-halamine structures as demonstrated in the FT-IR spectra of AN-co-ADMH and VAC-co-ADMH before and after bleach treatment, respectively. Before treatment, both of the two samples show a band at 1770 cm$^{-1}$, attributed to the amide structures of the hydantoin rings. After treatment, the 1770 cm$^{-1}$ band disappears, instead, a new band centered at 1784 cm$^{-1}$ can be detected. The 14 cm$^{-1}$ difference between the treated and untreated samples strongly suggests that the hydantoin structures are transformed into N-halamine structures. The N-halamine structures in all of the copolymers are very stable. After being immersed in distilled water for 2 months, the FT-IR spectra were re-recorded and no difference could be observed between the water treated and untreated N-halamines. After treatment with 0.1 mol/L sodium thiosulfate aqueous solution at 60° C. for 2 h, the N-halamine structures are converted to hydantoins, the 1784 cm$^{-1}$ bands changing back to 1770 cm$^{-1}$. However, after another bleach treatment, the 1770 cm$^{-1}$ band can be converted into 1784 cm$^{-1}$ again. The same "1784→1770→1784" cycle has been repeated 10 times, each time with the same result. Thus, the N-halamine structures possess durability and regenerability.

Example 5

This example illustrates the biocidal efficacy, durability and regenerability of the halogenated polymers by using the bacterium *Escherichia coli*.

The halogenated polymers were tested for biocidal efficacy by using the bacterium *Escherichia coli*. Samples in the form of films or powders were employed. The results are shown in Table 3. It can be clearly seen that all the halogenated copolymers demonstrate total kill against *Escherichia coli* at a flow rate of 0.2–0.6 mL/min for the powdered samples, and a contact time of less than 30 min for the film samples. No significant differences can be noticed in the antibacterial properties between different copolymers, indicating that the N-halamine structure in the halogenated copolymers provide the antibacterial activities.

TABLE 3

Antibacterial Properties of the Copolymers Against *E. Coli*

|  | AN-co-ADMH | AN-co-BADDD | MMA-co-ADMH | MMA-co-BADDD | VAC-co-ADMH | VAC-co-BADDD |
|---|---|---|---|---|---|---|
| Form of samples | powder | powder | powder | powder | film | film |
| E. Coli concentration (CFU/mL) | $10^6$ | $10^6$ | $10^5$ | $10^6$ | $10^6$ | $10^5$ |
| Flow speed for total kill (mL/min)* | 0.4 | 0.6 | 0.5 | 0.2 | X | X |
| Contact time for total kill (min)** | X | X | X | X | 15 | 25 |

*For powdered samples.
**For film samples.
* and ** Flow rate or contact time shown here are minimum conditions necessary for total kill of *E. Coli*.

The durability of the antibacterial properties of the copolymers was also studied. For all of the samples, after storage at 25° C. and 65% Relative Humidity for 3 months, antibacterial properties are essentially unchanged. VAC-co-ADMH films were also washed with distilled water, and after each wash, the antibacterial property was retested. Results are shown in Table 4. After different wash periods, the contact time necessary for a total kill of *E. coli* becomes longer and longer, indicating the decrease of antibacterial properties. On the other hand, the FT-IR spectra of the washed samples still show bands centered at 1784 cm–1, and no bands at 1770 cm$^{-1}$ can be detected, suggesting that the N-halamine structure remains almost unchanged upon washing.

TABLE 4

Relationship Between Wash Times(N) and Contact Time(T) Necessary for a total kill of *E. Coli* by VAC-co-ADMH Film (*E. Coli* concentration: $10^5$–$10^6$ CFU/mL)

| N | 0 | 3 | 5 | 10 | 15 |
|---|---|---|---|---|---|
| T (min) | 15 | 15 | 20 | 45 | 60 |

These findings are very likely due to the structure of the films. It has been pointed out that N-halamines kill microorganisms upon contact and films, unlike fibers and powders, have small surface areas. Upon washing, the N-halamines structures in the surface parts can be converted into hydantoins, but those in the bulk are unchanged.

Because the surface provides the antibacterial properties, the antibacterial properties decrease. However, after re-bleaching, the sample can provide a total kill at a contact time of 15 min again. And after 20 cycles of this "bleach→wash 10→times→re-bleach", the antibacterial properties of the sample are essentially unchanged, indicating that they are regenerable.

Example 6

This example illustrates the graft copolymerization procedure.

About 1 g of cotton was immersed in 30 mL of distilled water containing a known amount of ACN. The initiator was allowed to interact with cotton for 30 min and the ADM/AN mixture of known composition was added to the solution. The solution was stirred for a certain period of time at a known temperature. After the graft copolymerization, the cotton sample was taken out and extracted 3 times with 100 mL of hot DMF at 60° C. for 2 h to remove any un-grafted polymers. The cotton sample was then washed with large excess of distilled water, dried at 60° C. for 24 h, and stored in a desiccator for 72 h to reach constant weight.

Measurements

Percentage graft was calculated from the relation:

$$\% \text{ Grafting} = (W_2 - W_1)/W_1 \times 100$$

Where $W_1$ and $W_2$ are the weights of the original and the grafted cotton, respectively.

ADMH unit content in the grafted samples was calculated according to:

$$C_{ADMH} = 6.0 \times 10^{-3} \times (W_2 - W_1) \times \Phi_{ADMH}/W_1$$

Where $C_{ADMH}$ is the mole content of the ADMH unit in the grafted cotton, $6.0 \times 10^{-3}$ is the reciprocal of the molecular weight of the ADMH unit in the grafted copolymers, and $\Phi_{ADMH}$ is the weight fraction of ADMH unit in the grafted copolymers.

In a FT-IR spectra of cotton and an ADMH/AN grafted cotton, the 2243 cm$^{-1}$ band is attributed to $\nu$(CN) and the 1707 and 1770 cm$^{-1}$ bands can be assigned to the imide and amide structure, respectively. This is clear indication that ADMH/AN mixtures can be grafted onto cotton cellulose.

The fractional weight of the compound of Formula I such as ADMH, in the grafted copolymer can be calculated from the corresponding FT-IR spectra. For instance, in the FT-IR spectra of ADMH/polyacrylonitrile (PAN) physical mixtures, with increases in ADMH content, the intensity of the 1770 cm$^{-1}$ band increases, while that of the 2243 cm$^{-1}$ band decreases. In the plot of $A_{1770}/A_{2243}$ vs. $W_{ADMH}/W_{AN}$ ($A_{1770}$ and $A_{2243}$ represented the area of the 1770, 2243 cm$^{-1}$ band, and $W_{ADMH}$ and $W_{AN}$, the weight of ADMH and PAN in the physical mixtures, respectively), a linear relationship is obtained and the slope can be determined to be 0.74. Consequently, $\Phi_{ADMH}$, the weight content of the ADMH units in the grafted copolymers, could be calculated from Equation:

$$\Phi ADMH = 0.74 \times A_{1770}/(0.74 \times A_{1770} + A_{2243})$$

It should be kept in mind that because the graft copolymerization process is complicated, the graft copolymer is not well defined. Thus, this value ($\Phi_{ADMH}$ is the weight fraction of ADMH unit in the grafted copolymers.) is an "average" value. Nevertheless, this parameter works well in exploring the influence of reaction conditions on ADMH content, and this is very important in determining the antibacterial properties of the grafted samples, as can be seen in the next section, Example 7

This example illustrates grafting polyesters with monomers.

About 1 g of poly(ethylene terephthalate) (PET) fabric was immersed in 30 mL of distilled water containing a known amount (0.625–15% conc. of two in solution) of ADMH (90–50%) and triallyl-1,3,5-triazine-2,4,6-(1H,3H,5H)-trione (10–50%, as co-linker). The solution was heated to a known temperature (65–100° C.). A known amount of benzoyl peroxide (BPO) (0.125–1.5%) dissolved in an organic solvent (acetic acid, or acetone, or ethanol) was then added. Under constant stirring, the solution was kept at that temperature for a certain period of time (30 minutes to 3 hours). After the graft copolymerization, the PET sample was taken out and extracted 3 times with 100 mL of hot acetone at 60° C. for 2 h to remove any un-grafted polymers. The PET sample was then washed with large excess of distilled water, dried at 60° C. for 24 h, and stored in a desiccator for 72 h to reach constant weight. Yields were 2–30%, controllable.

Example 8

This example illustrates the antibacterial properties of the halogenated copolymers.

To transform hydantoin groups into N-halamine structures, the grafted cotton samples were bleached according to a method reported previously. (see, Sun, G. and Xu, X. *Textile Chem. Colorist,* 6:26 (1998).) Antibacterial properties of the bleached samples were evaluated against *Escherichia coli* according to AATCC Test Method 100, Durability and regeneration of the biocidal properties were tested with machine washing following AATCC Test Method 124. AATCC standard reference detergent WOB was used in all machine washing tests.

After treatment with CLOROX bleach, the amide groups of the grafted copolymers can be readily transformed into N-halamine structures. Before bleach treatment, the grafted sample shows a band at 1770 cm$^{-1}$ in the FT-IR spectrum attributed to the amide group of the hydantoin rings. After treatment, the 1770 cm$^{-1}$ band disappears, instead, a new band centered at 1782 cm$^{-1}$ can be detected. The 12 cm$^{-1}$ difference between the treated and untreated sample strongly suggests that the hydantoin structure has been transformed into N-halamine structures.

The stability of the N-halamine structure was also studied by using machine washing following AATCC Test Method 124. It was found that the N-halamine structures in the grafted cotton samples were stable up to 10 washes. After 15 washes, the N-halamine structure had been converted back to hydantoin, the 1782 cm$^{-1}$ bands changed back to 1770 cm$^{-1}$ However, after another bleach treatment, the 1770 cm$^{-1}$ band converted into 1782 cm$^{-1}$ again. The same "1782→1770→1782" cycle have been repeated 10 times, each with the same result.

The halogenated graft samples were tested for biocidal efficacy by using the bacterium *Escherichia coli* at a concentration of $10^6 \sim 10^7$ CFU/mL, following AATCC Test Method 100. The results are shown in Table 5. With the increasing of ADMH unit content in the grafted samples, the minimum contact time for a total kill of $10^6 \sim 10^7$ CFU/mL *E. coli* decreased. (Note the difference between sample 1 and sample 4), strongly indicating that it is the N-halamine structures in the grafted samples that provide the antibacterial properties.

TABLE 5

Antibacterial Properties of Some Halogenated Grafted Samples Against *E. Coli*\*

| Sample No. | Graft % | $C_{ADMH}$ (mol/g) | Wash Times** | Contact Time (min)*** |
|---|---|---|---|---|
| 1 | 15.2 | $3.4 \times 10^{-2}$ | 0 | 20 |
| 2 | 15.2 | $3.4 \times 10^{-2}$ | 10 | 30 |
| 3 | 15.2 | $3.4 \times 10^{-2}$ | 20 | 180 |
| 4 | 26.4 | $9.0 \times 10^{-2}$ | 0 | 10 |
| 5 | 26.4 | $9.0 \times 10^{-2}$ | 20 | 60 |

\*Antibacterial properties were tested according to AATCC Test Methods 100. *E Coli concentration*: $10^6 \sim 10^7$ CFU/mL.
\*\*Machine washing, following AATCC Test Methods 124, AATCC standard reference detergent WOB was used in all of the machine washing tests.
\*\*\*Minimum contact time for a total kill.

The durability of the antibacterial properties of the grafted samples has studied. After 10 washes, the contact time necessary for a total kill of *E. coli* was relatively unchanged, indicating the stability of the N-halamine structures. However, further washes converted the N-halamine structures to hydantoins and the minimum contact time for a total kill gone up as the antibacterial properties decreased (see Table I, sample 2, 3, and 5). However, after re-bleaching, the sample again provided total kill at a contact time of less than 30 min. And after 10 these "bleach wash 10 times→re-bleach" cycles, the antibacterial properties of the samples were unchanged, indicating the antibacterial properties were regenerable.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound selected from the group consisting of

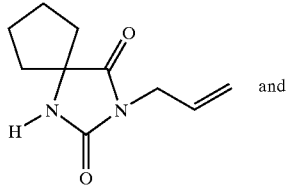 and

-continued

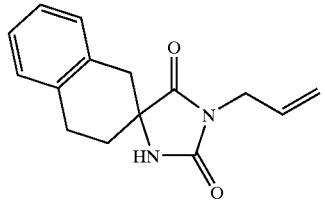

2. A compound having the formula:

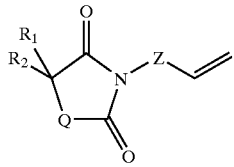

wherein:

$R^1$ and $R^2$ and the carbon to which they are bound join to form a carbocyclic ring; wherein said carbocyclic ring is cyclopentane;

Q is a member selected from the group consisting of NH, and N—$R^9$, wherein $R^9$ is a halogen; and Z is optionally substituted ($C_1$–$C_3$)alkylene.

3. The compound of claim 2, wherein $R^9$ is chloro.
4. The compound of claim 2, wherein $R^9$ is bromo.
5. The compound of claim 2, wherein $R^9$ is fluoro.
6. The compound of claim 2, wherein $R^9$ is iodo.
7. The compound of claim 2, wherein Q is NH.
8. The compound of claim 2 wherein Z is methylene.
9. A compound wherein said compound is

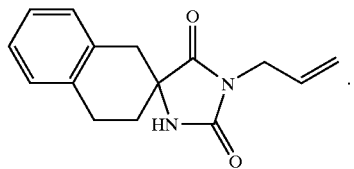

\* \* \* \* \*